United States Patent [19]

Foxman

[11] Patent Number: 4,844,965
[45] Date of Patent: Jul. 4, 1989

[54] ABSORPTIVE DEVICE FOR INCONTINENT PATIENTS

[75] Inventor: Charles Foxman, St. Louis, Mo.

[73] Assignee: Medtex Products, Inc., St. Louis, Mo.

[21] Appl. No.: 148,023

[22] Filed: Jan. 25, 1988

[51] Int. Cl.[4] .............................................. B32B 33/00
[52] U.S. Cl. .......................................... 428/91; 5/484;
428/121; 428/192; 428/193; 428/198; 428/284;
428/286; 428/246; 428/247; 428/296; 428/913;
604/380
[58] Field of Search .................... 5/484; 604/366, 370,
604/372, 378, 380; 428/296, 286, 284, 192, 193,
198, 913, 246, 247, 88, 91, 121

[56] References Cited

U.S. PATENT DOCUMENTS

| 4,610,352 | 9/1986 | Howey et al. | 428/296 |
| 4,655,877 | 4/1987 | Horimoto et al. | 428/296 |
| 4,659,614 | 4/1987 | Vitale | 428/296 |

Primary Examiner—James J. Bell
Attorney, Agent, or Firm—Polster, Polster and Lucchesi

[57] ABSTRACT

An absorptive device for incontinent patients is disclosed as including a liquid permeable absorptive member having an outer facing layer of synthetic fabric and an inner backing layer of fabric having a blend of thermal plastic and cellulosic fibers, the synthetic outer facing layer being ultrasonically welded to the thermal plastic fibers of the blended material inner backing layer, and a liquid impervious barrier member underlying the liquid permeable absorptive member to restrict the flow of liquid therethrough. The ultrasonic welding is performed at intermittent locations in a predetermined configuration representing a quilt pattern. A liquid impervious side binding member overlaps and binds the free end and immediately adjacent surfaces of the absorptive and barrier members to inhibit side leakage. The liquid impervious barrier member includes a thermal plastic film of liquid impervious material sandwiched between two fabrics which are then bonded to one another.

7 Claims, 2 Drawing Sheets

ABSORPTIVE DEVICE FOR INCONTINENT PATIENTS

BACKGROUND OF THE INVENTION

This invention relates to absorptive devices for incontinent patients, and in particular, to re-useable moisture impervious incontinent pads of the type used in hospitals, nursing homes and other similar institutions. Absorptive devices for incontinent patients can also include individual products worn by the patient. Individual, patient worn products are typically disposable, and therefore, in the discussion that is to follow, attention will be focused on incontinent pads used with beds or chairs, which are considered the principal area of use of the present invention.

Typically, absorptive devices as incontinent pads have fallen into two categories. One has been made of synthetic and is disposable after one use. This minimizes labor involved in washing and drying, but also is comparatively expensive. The other category of product is a natural fabric, combination natural/synthetic fabric, or entirely synthetic product which is re-useable. The present invention is directed to this second category of products, as will become apparent.

By definition, a re-useable pad means that it is also capable of being washed and dried numerous times. Therefore, it is important to have as many washings and dryings of the product as possible in order to keep the cost per use as low as possible. Most of the natural fabric, or combination natural/synthetic fabric pads developed to date unfortunately degrade rapidly during the washing and drying process, and therefore, are useful for a shorter period of time. Most of such products have, therefore, not been long-lasting. During use, such products must not only avoid prior contamination, they must facilitate patient comfort and use, all without great initial cost per unit to the user. While there have been many efforts to develop such a product, to the best of applicant's knowledge, none has been forthcoming which overcomes the aforenoted and other deficiencies until the development of the present invention.

SUMMARY OF THE INVENTION

Among the several objects and advantages of the present invention include:

An absorptive device in which the layers of a liquid permeable absorptive member are ultrasonically welded together in a predetermined intermittent configuration to durably fasten and hold the layers together while allowing liquid communication throughout the layers.

An absorptive device of the type described which includes a liquid impervious barrier member underlying the liquid permeable absorptive member and a liquid impervious side binding member which binds the absorptive and barrier members to one another to inhibit leakage of liquid received within the confines of the absorptive device.

An absorptive device of the type described in which the liquid impervious barrier member includes a thermal plastic film of liquid impervious material sandwiched between two fabrics which are then bonded to one another. The sandwich effect prevents the thermal plastic film from folding back upon and sticking to itself during the washing and drying process of laundering.

An absorptive device as described above which has soft patient contacting surfaces and a bed or chair contacting surface which inhibits slipping relative to the bed or chair, as well as "shifting" or "bunching" of the absorptive device during patient movement.

An absorptive device of the type described which is considerably lighter in weight than natural fabric products to provide quicker drying time at lower temperatures, is wrinkle resistant and requires little or no ironing, is hypoallergenic, lasts twice as long as natural fabric products, is odor and mildew resistant, is bacterial and fungal resistant, and meets government specifications for flame resistance.

The foregoing and other objects and advantages are achieved by an absorptive member having an outer facing layer of thermal plastic material and an inner facing layer which has a material blend of thermal plastic and cellulosic fibers, the synthetic outer facing layer being ultrasonically welded to the thermal plastic fibers of the blended material inner backing layer, and a liquid impervious barrier member underlying the liquid permeable absorptive member to restrict the flow of liquid therethrough. The synthetic outer facing layer is ultrasonically welded to the thermal plastic fibers of the blended material inner backing member at intermittent locations in a predetermined configuration representing a quilt pattern throughout. A liquid impervious side binding member overlaps and binds the free end and immediately adjacent surfaces of the liquid permeable absorptive member and the liquid impervious barrier member to inhibit side liquid leakage. The liquid impervious member includes a thermal plastic film of liquid impervious material sandwiched between two fabrics which are then bonded to one another. The outer facing layer of the liquid permeable absorptive member and the outer membrane of the liquid impervious barrier member are each formed from fabric that provides soft patient comfort surfaces. In addition, the fabric of the outer membrane of the liquid impervious barrier member is napped to aid in resisting slipping or bunching of the device on surfaces.

The above and other objects and advantages of the present invention will become apparent from the ensuing description.

DESCRIPTION OF THE PREFERRED EMBODIMENT

Figure 1:
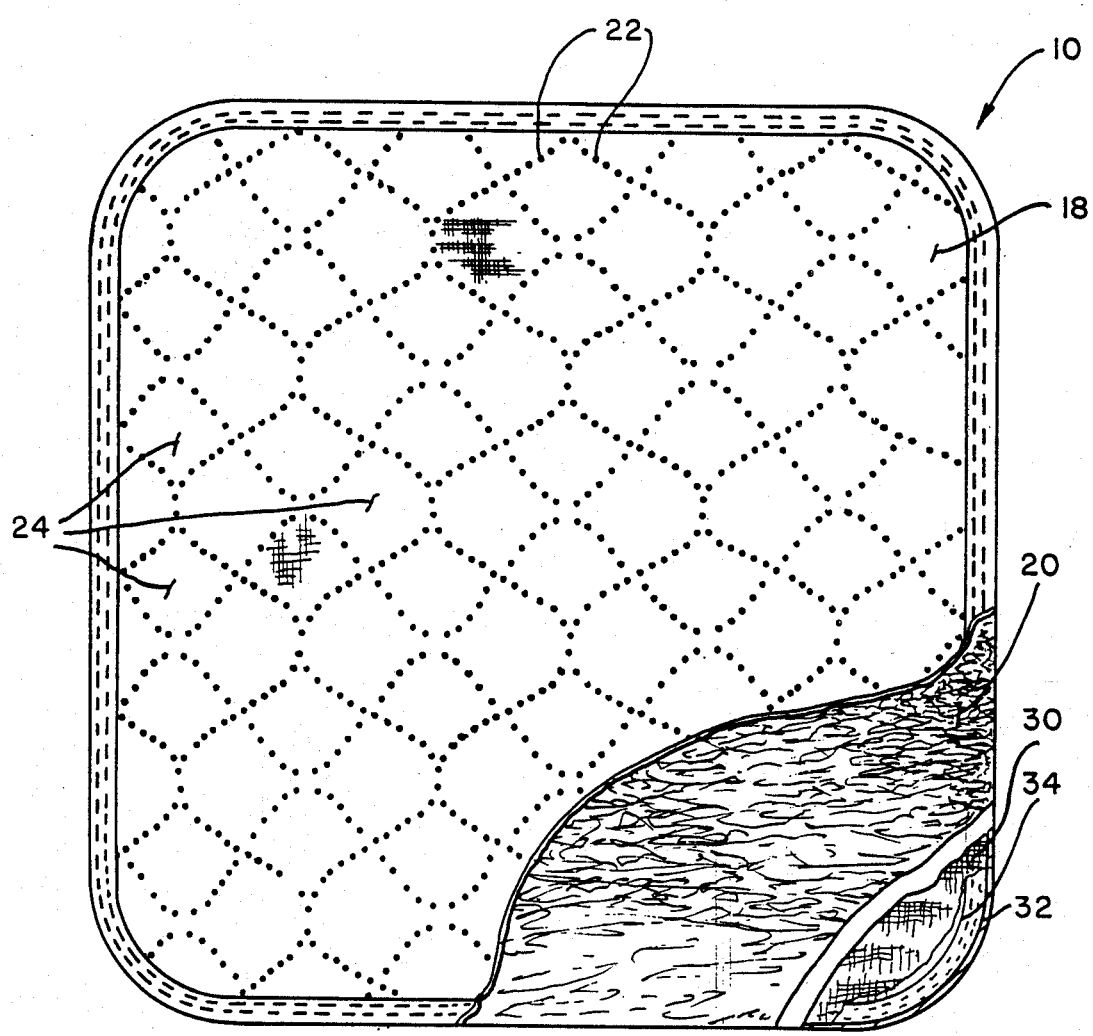
FIG. 1 is a top view of an absorptive device for incontinent patients which is constructed in accordance with the teachings of the present invention, in which the lower rght hand corner thereof has been exposed to reveal the various layers and membranes of the absorptive device.

Referring now to the drawings, an absorptive device for incontinent patients is generally identified by numeral 10 in the drawings. As best seen in FIGS. 3-6 of the drawings, the absorptive device 10 includes a liquid permeable absorptive member 12, a liquid impervious barrier member 14, and a liquid impervious side binding member 16, which are constructed and assembled to one another in a manner now to be described.

The liquid permeable absorptive member 12 includes an outer facing layer of synthetic fabric 18 and an inner backing layer 20 with a material blend of thermal plastic and cellulosic fibers. The outer facing layer 18 is manufactured from a 100% synthetic thermal plastic fabric. The outer facing layer 18 is manufactured to provide a soft surface that breathes, enhancing patient comfort. The inner backing layer 20 of the liquid permeable absorptive member 12 is a blend of thermal plastic and cellulosic fibers which are aligned and punched with needles to gain material integrity. This blend of material fibers is important in that it not only absorbs liquid quite readily, but permits the outer facing layer of material to be ultrasonically welded to the thermal plastic fibers of the inner backing layer.

The outer facing layer 18 of synthetic thermal plastic fibers and the inner backing layer 20, with a material blend of synthetic thermal plastic and cellulosic fibers, may be formed either as woven or non-woven layers, as desired, although preferably both of such layers are non-woven layers having their fibers connected as shown in the various figures of the drawings.

Figure 2:
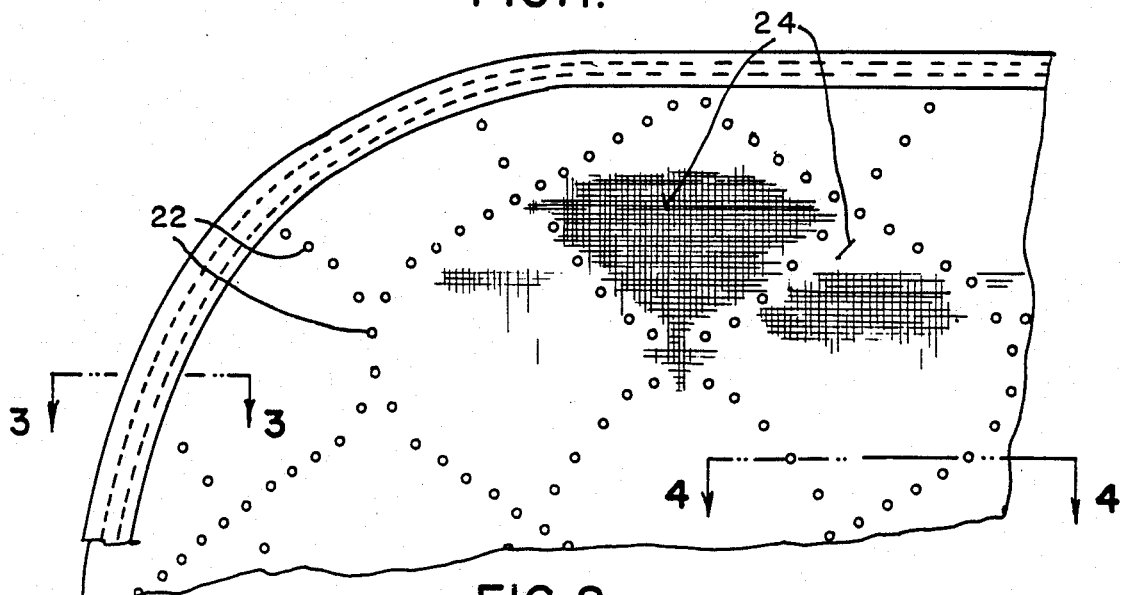
FIG. 2 is an enlarged fragmentary top view of the absorptive device for incontinent patients shown in FIG. 1.
Figure 4:
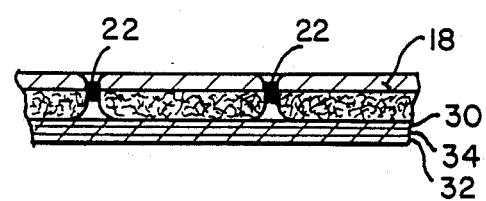
FIG. 4 is an enlarged fragmentary sectional view taken along lines 4—4 of FIG. 2.
Figure 5:
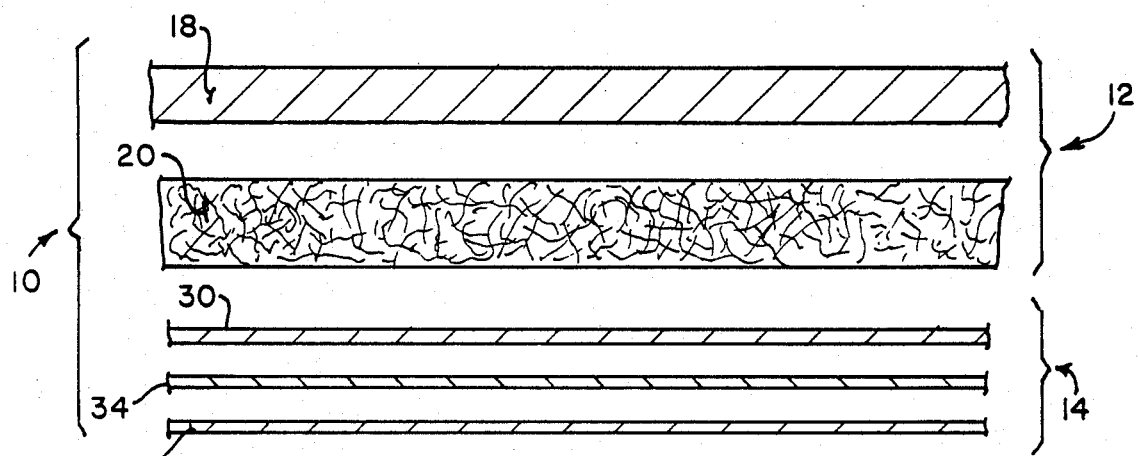
FIG. 5 is an exploded side elevational sectional view showing the various layers and membranes comprising the absorptive device for incontinent patients of the present invention.
Figure 6:
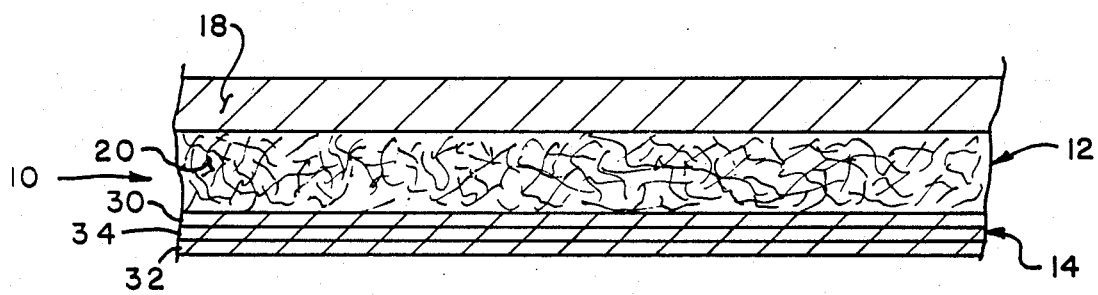
FIG. 6 is a side elevational sectional view showing the layers and membranes of the absorptive device when assembled to one another for use.

The ultrasonic welding of the layers 18, 20 is best seen in FIGS. 1-2 and 4 of the drawings. There, it will be seen that the thermal plastic fibers of the inner backing layer 20 are ultrasonically welded to the closely spaced, intersecting strands of thermal plastic material, at intermittent locations 22 which have a predetermined configuration representing a quilt pattern 24 throughout the absorptive device 10. The heat and pressure applied during the ultrasonic welding process must be such as to cause melting and subsequent bonding of the two layers 18, 20 to one another at the series of intermittent locations 22 as shown in the drawings. Each of the intermittent locations 22 is represented by a small circular welded area, and is to be understood as to constitute a bond between the synthetic thermal plastic fabric of the outer layer 18 and the thermal plastic fibers of the material blend in the inner backing layer 20. As a result, the ultrasonic welding coupled with the simulated quilt pattern produces a "threadless quilting" in which the outer facing layer 18 and the inner backing layer 20 are fastened and supported by one another. At the same time, the intermittent locations of the ultrasonic welds 22 allows a liquid communication throughout the layers 18, 20 in the absorptive device 10.

The liquid impervious barrier member 14 includes an inner membrane 30 adjacent to the blended material inner backing layer 20, an outer membrane 32 spaced from the layer 20, and an interposed thermal plastic film membrane 34. The inner membrane 30 is made from a synthetic scrim fabric which prevents the liquid impervious barrier member from sticking to itself when subject to high temperatures, such as would be found in commercial dryers. The outer membrane 32 is formed from a thermal plastic fabric which not only protects the membranes and layers positioned within the confines of the absorptive device 10, but which is preferably a napped fabric which will not allow the absorptive device 10 to "slip or slide" on a chair of bed, while at the same time, maintaining a neat appearance by avoiding "shifting or bunching" of the absorptive device 10 during patient movement. The interposed thermal plastic film membrane 34 is specially formulated to adhere when heat and pressure are applied and then cured to produce the liquid impervious barrier member 14 so as to achieve a bonding integrity and withstand a minimum of 200 launderings and a minimum melt point of 400° F.

Figure 3:
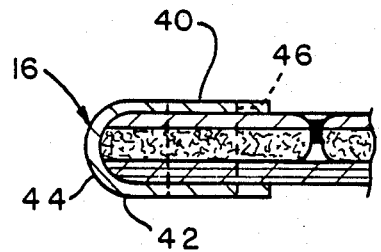
FIG. 3 is a fragmentary enlarged sectional view taken along lines 3—3 of FIG. 2.

In order to hold the absorptive and barrier members 12, 14 respectively, to one another along the outer free ends thereof as well as prevent side liquid leakage, the liquid impervious side binding member 16 is provided. This is best shown in FIG. 3 of the drawings where it will be seen that the side binding member 16 comprises a generally U-shaped design having upper and lower leg portions 40, 42 which are connected together by the bight or end portion 44. When mounted as shown in FIGS. 1 and 3 of the drawings, along the free end surfaces and immediately adjacent outwardly facing surface portions of the absorptive and barrier members 12, 14, a double needle lock stitch 46 can be used to bind and secure the upper and lower legs 42 of the side binding member 16 to the absorptive and barrier members 12, 14 respectively. Preferably, the side binding member 16 is made from the same construction as the liquid impervious barrier member 14. Thus, liquid received within the absorptive device 10 will be retained within the confines thereof without pass-through or side leakage.

With an absorptive device 10 constructed in the manner just described, the inner facing layer 30 of the liquid impervious layer and the outer facing layer 32 of the liquid impervious layer, protects the sandwiched liquid impervious membrane 34 from dryer heat which would cause this layer to stick to itself, unless sandwiched between the aforementioned components. As explained above, this synthetic material blend inner backing layer 20 is quite absorptive, while permitting ultrasonic welding with the outer facing layer 18 as described. In addition, the synthetic product materials from which the absorptive device 10 is made are considerably lighter in weight than natural fabric products providing quicker drying time at lower temperatures. This results in obvious energy and time dollars saved during processing of the absorptive device. The synthetic materials of the absorptive device 10 also are wrinkle resistant and require little or no ironing, are hypoallergenic, last considerably longer than natural fabric products, are odor and mildew resistant, are bacterial and fungal resistant, have soil release characteristics, and meet government specifications for flame resistance. In view of the above, it will be seen that the present invention discloses an absorptive device for incontinent patients which achieves the objects of the invention and produces many other advantageous results as well.

As various changes could be made in the above constructions without departing from the scope of the invention, it is intended that all matter contained in the above description or shown in the accompanying drawings shall be interpreted as illustrative and not in a limiting sense.

Having thus described the invention, what is claimed and desired to be secured by Letters Patent is:

1. An absorptive device for incontinent patients comprising a liquid permeable absorptive member having an outer facing layer of interconnected synthetic thermal plastic fibers and an inner backing layer with a material blend of interconnected synthetic thermal plastic and cellulosic fibers, the synthetic thermal plastic fibers of outer facing layer being ultrasonically welded to the synthetic thermal plastic fibers of the blended material inner backing layer to join the layers together while allowing liquid communication throughout the layers, the synthetic thermal plastic fibers of the outer facing layer being ultrasonically welded to the thermal plastic fibers of the blended material inner backing layer at intermittent locations in a predetermined configuration representing a quilt pattern throughout, a liquid impervious barrier member underlying the liquid permeable absorptive member to restrict the flow of liquid therethrough, and a liquid impervious side binding member which overlaps and binds the liquid permeable absorptive member and liquid impervious barrier member to one another along free end surfaces thereof and also including outwardly facing surface portions immediately adjacent to said free end surfaces to inhibit side leakage of liquid.

2. The absorptive device as defined in claim 1 wherein the liquid impervious barrier member includes a thermal plastic film of liquid impervious material sandwiched between two fabrics bonded together by the application of heat, pressure and curing.

3. The absorptive device as defined in claim 2 wherein the outer facing layer of the liquid permeable absorptive member and the outer membrane of the liquid impervious barrier member are each formed from a synthetic thermal plastic fabric, and said inner and outer membranes of the liquid impervious barrier member are heat and pressure bonded together after a thermal plastic film membrane is interposed therebetween.

4. An absorptive device for incontinent patients comprising a liquid permeable absorptive member having an outer facing layer of interconnected synthetic thermal plastic fibers and an inner backing layer having a material blend of interconnected synthetic thermal plastic and cellulosic fibers, the synthetic thermal plastic fibers of the outer facing layer being ultrasonically welded to the thermal plastic fibers of the blended material inner backing layer at intermittent locations in a predetermined configuration representing a quilt pattern throughout, a liquid impervious barrier member underlying the liquid permeable absorptive member, and a liquid impervious side binding member which overlaps and binds the liquid permeable absorptive member and liquid impervious barrier member to one another along free end surfaces and immediately adjacent outwardly facing surface portions thereof, the liquid impervious barrier member and liquid impervious side binding member both being formed of a thermal plastic film of liquid impervious material sandwiched between two fabrics and bonded together by heat, pressure and curing.

5. The absorptive device as defined in claim 4 wherein the outer facing layer of the liquid permeable absorptive member is made from a synthetic thermal plastic fabric manufactured with a soft surface for patient comfort.

6. The absorptive device as defined in claim 5 wherein the outer membrane of the liquid impervious barrier member is made from a synthetic thermal plastic napped fabric to aid in resisting slipping or bunching of the device on surfaces.

7. The absorptive device as defined in claim 5 wherein the synthetic thermal plastic fibers of the outer facing layer of the liquid permeable absorptive member includes a plurality of closely spaced, intersecting and interconnected generally longitudinally and transversely directed strands of thermal plaetic material, said intermittent ultrasonically welded locations including said intersecting strands of thermal plastic material of the outer facing layer and the thermal plastic fibers of the blended material inner backing layer.

* * * * *